United States Patent [19]

Borghi

[11] Patent Number: 5,800,524
[45] Date of Patent: Sep. 1, 1998

[54] PROSTHESIS WITH SPIRAL STITCHING ELEMENT

[75] Inventor: Enzo Borghi, Budrio, Italy

[73] Assignee: Bard Galway Limited, Galway, Ireland

[21] Appl. No.: 849,681

[22] PCT Filed: Dec. 13, 1995

[86] PCT No.: PCT/IT95/00218

§ 371 Date: Jun. 12, 1997

§ 102(e) Date: Jun. 12, 1997

[87] PCT Pub. No.: WO96/18360

PCT Pub. Date: Jun. 20, 1996

[30] Foreign Application Priority Data

Dec. 16, 1994 [IT] Italy ............... BO94A0552

[51] Int. Cl.$^6$ .................... A61F 2/06
[52] U.S. Cl. .............. 623/1; 623/12; 606/153; 606/198
[58] Field of Search .......... 623/1, 12; 606/153, 606/191, 198

[56] References Cited

U.S. PATENT DOCUMENTS

| | | |
|---|---|---|
| 3,774,615 | 11/1973 | Lim et al. ............... 606/153 |
| 4,190,909 | 3/1980 | Ablaza . |
| 4,368,736 | 1/1983 | Kaster . |
| 4,769,029 | 9/1988 | Patel ............... 623/1 |
| 5,127,413 | 7/1992 | Ebert . |
| 5,330,490 | 7/1994 | Wilk et al. ............... 623/1 |

FOREIGN PATENT DOCUMENTS

| | | |
|---|---|---|
| 0326426 | 8/1989 | European Pat. Off. . |
| 0664107 | 7/1995 | European Pat. Off. . |
| 4304353 | 4/1994 | Germany . |
| 2269104 | 2/1994 | United Kingdom . |

OTHER PUBLICATIONS

Abstract of SU-176 4094 to Emelyanov, Dated Aug. 1992.

*Primary Examiner*—Paul B. Prebilic

[57] ABSTRACT

A prosthesis for a blood vessel comprises an implantable tubular cylindrical element of biocompatible material, affording a pair of rigid rings positioned one at either end, that can be inserted into a diseased section of the opened vessel with the rings offered in direct contact to corresponding healthy cylindrical portions, also, a pair of first spiral wound locating elements respectively associated with and encircling the rings through a circumferential distance of no less than 360°, each of which is ensheathed freely in its turn by a second spiral wound stitching element having a sharp point; the second spiral wound element is rotated helically about the first spiral wound element and caused thus to advance along its own longitudinal axis, with the result that the rigid ring becomes securely anchored as the point penetrates the wall of the vessel, progressively pinning the cylindrical portion to a given depth between the two spiral wound elements.

11 Claims, 4 Drawing Sheets

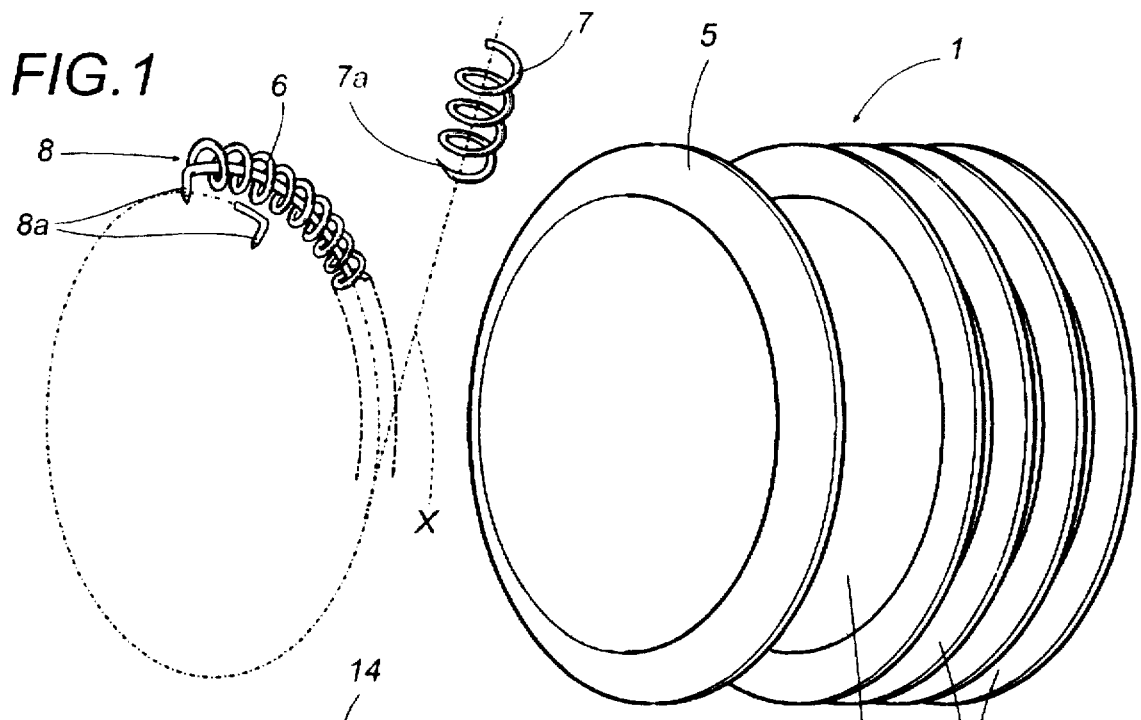
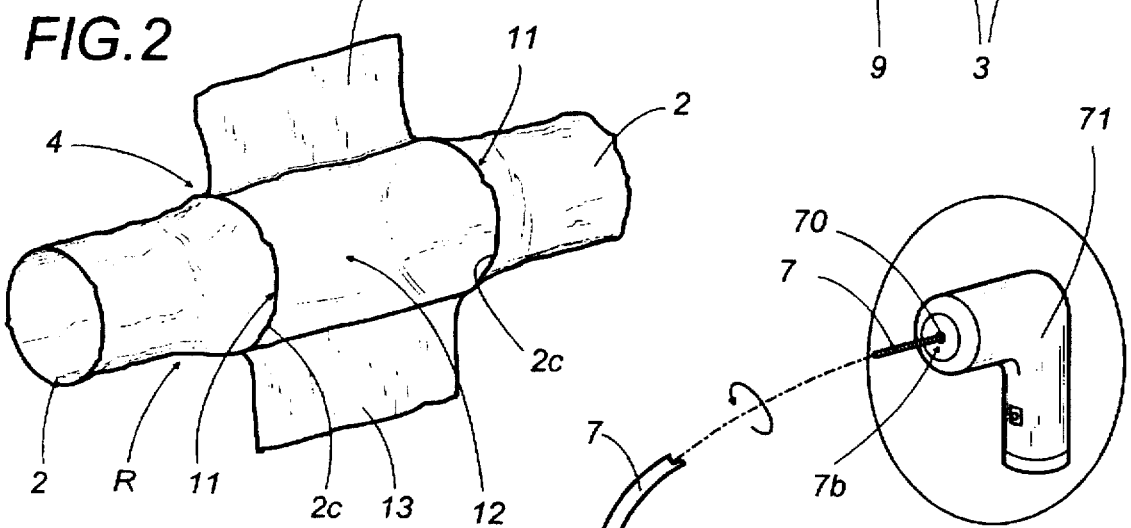
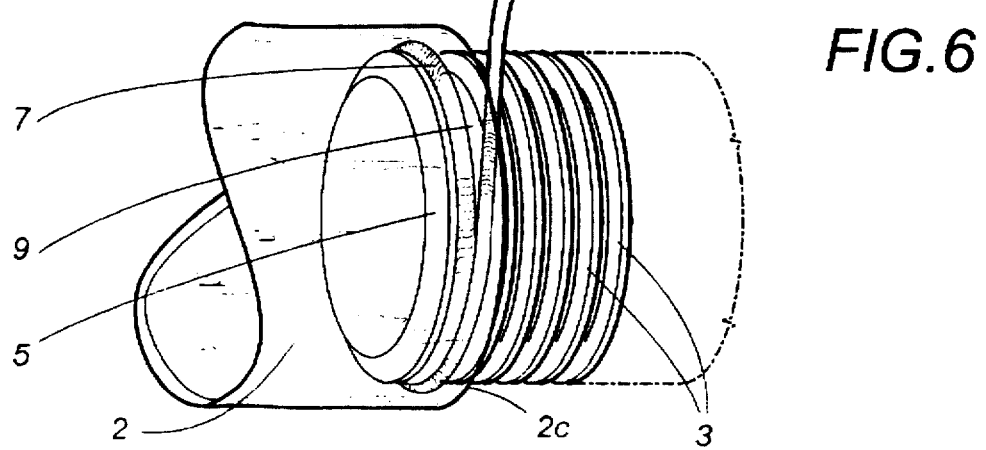

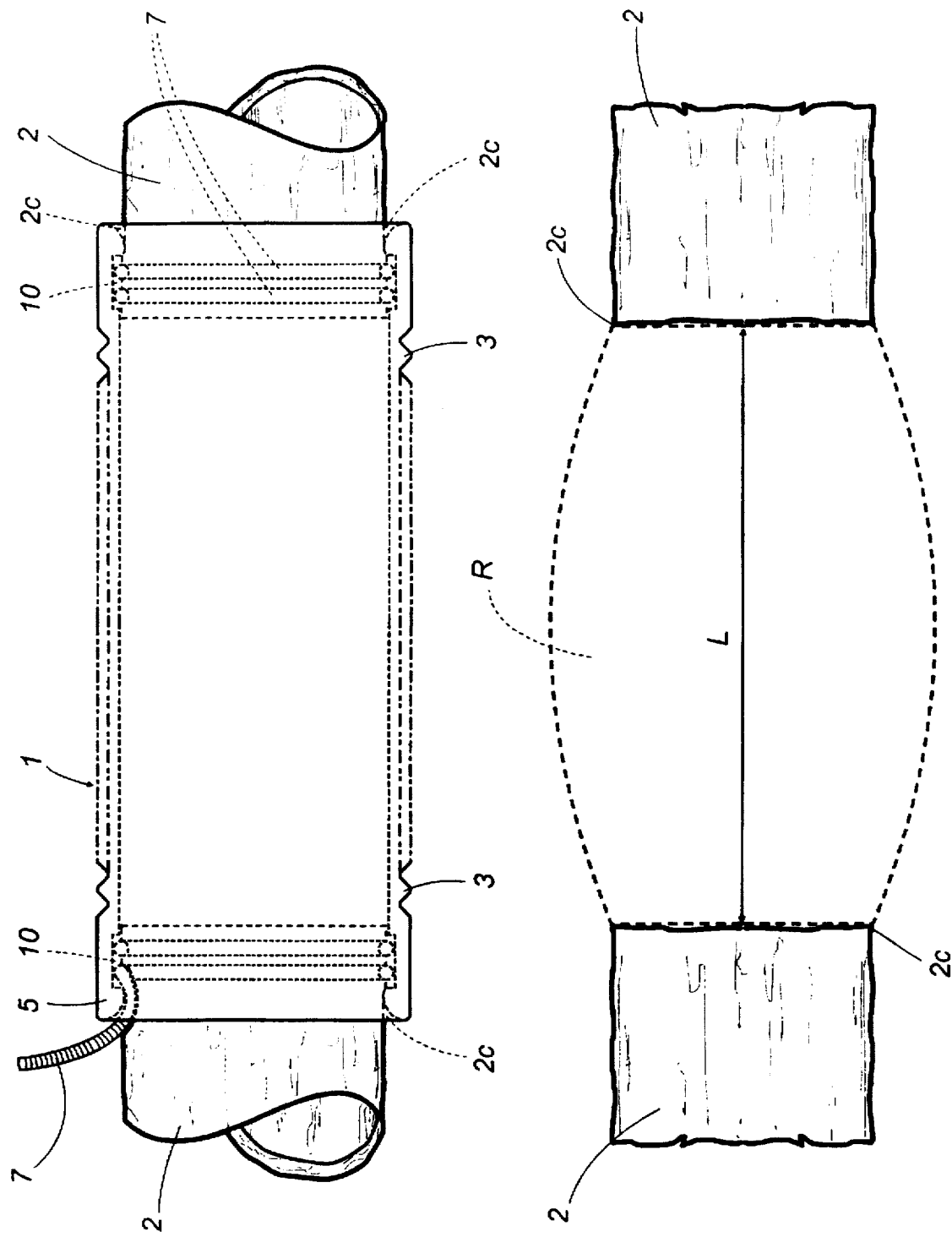

PROSTHESIS WITH SPIRAL STITCHING ELEMENT

This application is a national stage application pursuant to 35 U.S.C. §371 of PCT/IT95/00218 filed Dec. 13, 1995.

TECHNICAL FIELD

The present invention relates to a prosthesis for blood vessels.

At present, prostheses of this particular type consist in a portion of tube fashioned from a biocompatible material and implanted in the body of a patient diagnosed as suffering from an aneurysm.

Aneurysm is the name given in the field of medicine to localized swellings that occur in the walls of blood vessels; such swellings are encountered particularly in the aorta, along the part between the lung wall and the femoral region. If aneurysm is not diagnosed early, the walls of the blood vessel affected by the swelling may rupture hazardously, and possibly cause bleeding from the vessel.

BACKGROUND ART

Such ruptures are prevented by a surgical operation of which the initial step consists in making a longitudinal incision along the middle of the sac produced by the swelling of the aorta wall and removing the blood clot that will have formed within the passage; thereafter, further incisions are made circumferentially (extending in length some two thirds of the circumference presented by the aorta) to coincide with the points where the sac meets healthy tissue on either side.

The incisions serve in this manner to create two flaps resembling a pair of doors, affording access to the inside of the aorta, through which the surgeon proceeds to insert the aforementioned prosthesis of biocompatible material in such a way that its two ends are disposed in contact with respective cylindrical terminating portions of the aorta on either side of the open section; with the prosthesis in place, the ends are secured internally of the respective cylindrical portions by sutures. Finally, the two flaps are flattened against the already anchored prosthesis and sutured so that the wall of the aorta remains permanently associated with the prosthesis.

This type of surgery is lengthy and laborious (typically requiring two to three hours at least), and has a markedly low rate of success (no more than 25% according to published research data). The length of the operation dictates that circulation must be diverted outside the body, a necessity that brings its own well-documented consequences, whilst the low success rate is also due to the fact that the sutures are performed manually by the surgeon utilizing traditional means (needle and biocompatible thread) which can neither guarantee a faultless mechanical closure, nor ensure that the flow of blood through the joined portions of the prosthesis and the aorta will be fully contained over time, since the closure consists in no more than discrete points of contact where the biocompatible suture simply "pinches" the wall of the vessel against the prosthesis.

DISCLOSURE OF THE INVENTION

The object of the present invention is to set forth a prosthesis for blood vessels structured in such a way as to enable a simple and swiftly accomplished implant, guaranteed efficient both from the mechanical standpoint and from that of its ability to contain the flow of blood, for which the overall operating time is notably shorter than that mentioned above.

The invention will now be described in detail, by way of example, with the aid of the accompanying drawings, in which:

FIG. 1 is an exploded illustration of the prosthesis for a blood vessel according to the present invention, viewed in perspective;

FIGS. 2 and 3 illustrate two steps in a procedure by which the prosthesis of FIG. 1 is inserted and implanted in a blood vessel, the one viewed in perspective and the other in a side elevation with certain parts omitted;

FIG. 6 shows a further step in the procedure of inserting and implanting the prosthesis of FIG. 1, namely securing the prosthesis to the blood vessel, illustrated in perspective with certain parts omitted better to reveal others;

FIGS. 7, 7a and 8 show respective steps in an alternative method of inserting and implanting the prosthesis according to the invention, all of which illustrated in side elevation with certain parts omitted.

Figure 3:
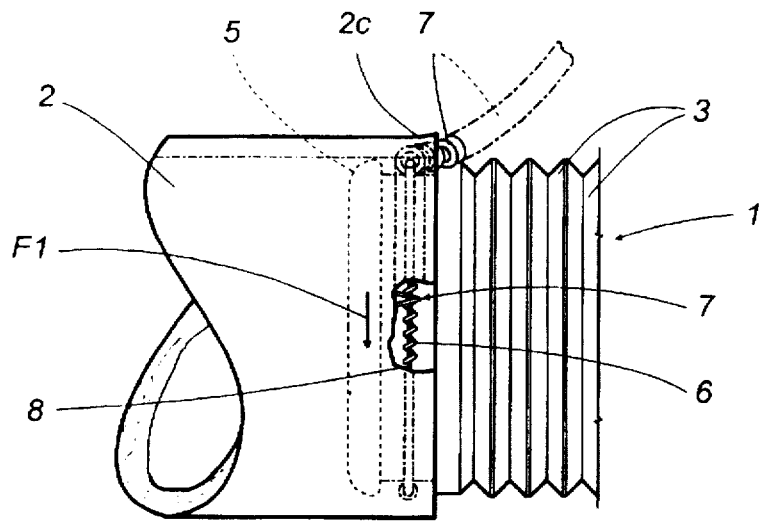

Referring to the figures of the accompanying drawings, and in particular to FIG. 1, the present invention relates to a prosthesis (denoted 1 in its entirety) implantable in a section 4 of a blood vessel 2 and comprising: a tubular cylindrical element 3, a pair of first spiral wound guide and locating elements 6, also a pair of respective second spiral wound stitching elements 7.

The tubular cylindrical element 3 is to all intents and purposes a flexible sleeve fashioned from a biocompatible material, for example Dacron™ (a proprietary polyester fibre made by Du Pont de Nemours, USA), such as can be implanted in a section 4 of a blood vessel 2 laid open as illustrated in FIG. 2 (the procedure to be described in due course).

The sleeve 3 comprises a pair of first rigid rings 5 located one at each end and embodied integrally with the tubular structure, such as can be offered in direct contact to cylindrical portions 2c of the blood vessel 2, and it is with these same first rigid rings 5 that the aforementioned first spiral wound guide and locating elements 6 (likewise fashioned from a biocompatible material) are associated; more precisely, each first spiral wound element 6 ensheaths and remains permanently associated with a filiform element 8 or second ring which in turn encircles an external portion of the relative first rigid ring 5, occupying a circumferential channel denoted 9. The filiform element 8 can be anchored by one end 8a, which is bent inwards and insertable thus into a socket 15 afforded by the first ring 5.

Similarly, in an alternative solution (see also FIGS. 7 and 8), each first spiral wound element 6 ensheaths and is permanently associated likewise with a filiform element 8 or second ring similar to that described previously, though in this instance extending circumferentially around an internal portion of the first rigid ring 5, occupying an inward-facing circumferential channel 10.

Each first spiral wound element 6 is ensheathed in turn by the relative second or stitching spiral wound element 7, which again will be fashioned in a biocompatible material; this same second element 7 is embodied with a sharp point 7a and proportioned such that when rotated helically around the respective first spiral wound element 6 and caused thus to advance along its own longitudinal axis X, the first rigid ring 5 will be secured circumferentially and continuously to the relative cylindrical portion 2c of the blood vessel 2: as the point is rotated, in effect, a given thickness S of the cylindrical portion 2c will become interposed between the two spiral wound elements 6 and 7.

Figure 4:
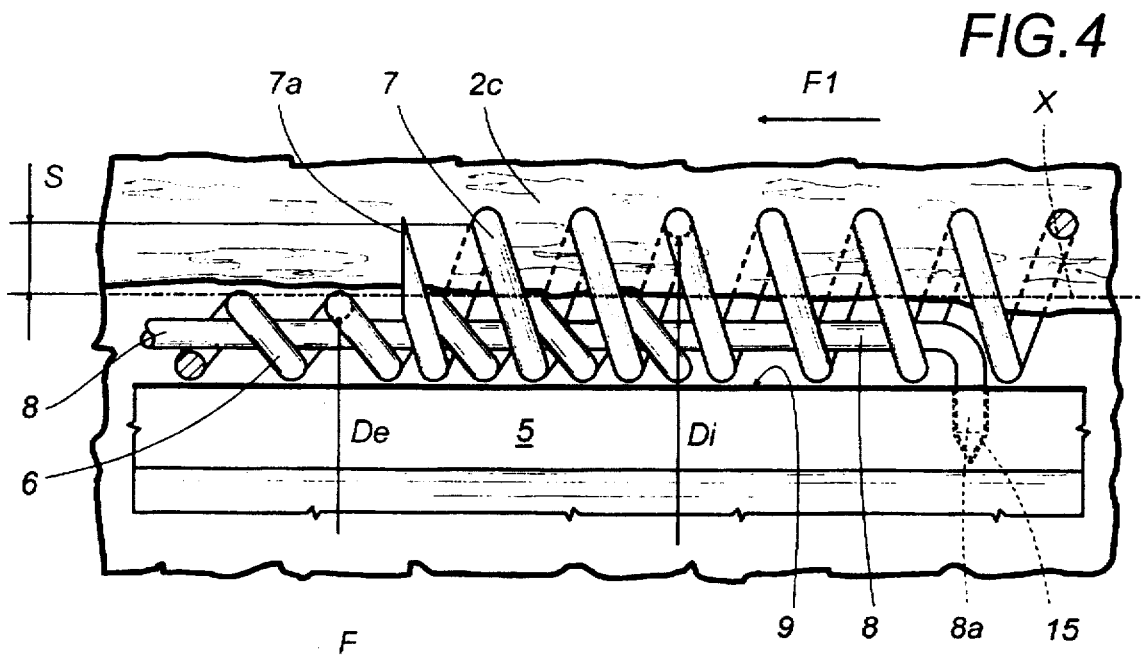
FIGS. 4 and 5 are respective details of FIG. 3, seen enlarged and partly in section, illustrating the step of securing two spiral wound elements to the blood vessel.
Figure 5:
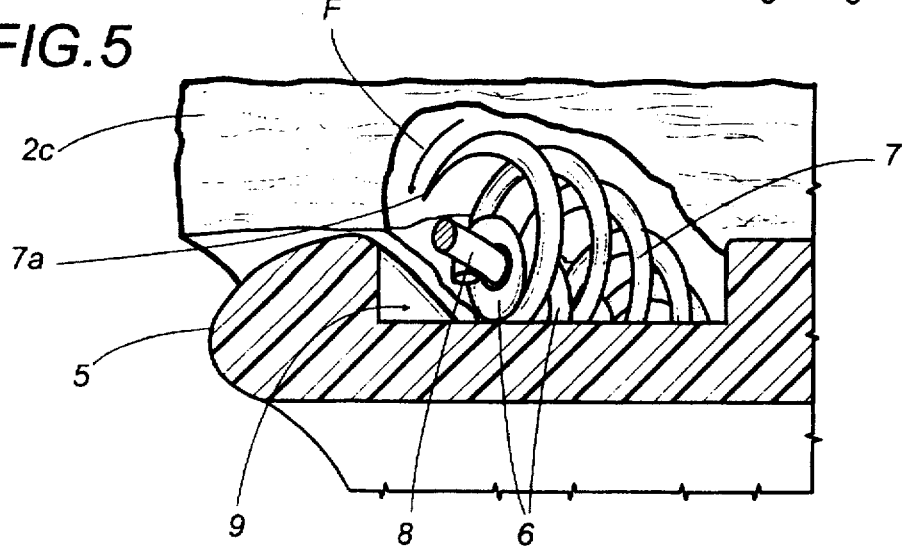

In practice (see FIG. 4), the internal diameter Di of the second spiral wound element 7 is greater than the external diameter De of the respective first spiral wound element 6, and the second spiral wound element 7 functions exactly in the manner of a worm or lead screw, winding around and at the same time advancing along the first spiral wound element 6 in such a way as to pierce, or rather "stitch" the wall of the cylindrical portion 2c (see arrow F) to a given depth S, from either the inside or the outside. Accordingly, a portion of the blood vessel 2 remains pinned to this same depth S, which corresponds to the difference between the two aforementioned diameters Di and De, by a continuous succession of stitches of which the frequency or gauge is determined by the distance between successive single coils of the second spiral wound element 7. The result is to establish a permanent association between the first rigid ring 5 and the cylindrical portion 2c of the blood vessel 2.

The present invention also relates to a method by which the prosthesis 1 is inserted into a blood vessel 2 affected with a localized swelling R and the aforementioned permanent association duly obtained, which comprises a succession of steps now to be described (see FIGS. 2, 3 and 6).

In a first solution, which utilizes first spiral wound elements 6 located externally of the first rigid rings 5, the steps are those of:

a) making incisions in the blood vessel 2 at the site of the swelling R both longitudinally and around some two thirds of the circumference of the vessel at the respective areas of contact 11 between the swelling R and the healthy stretches on either side, in such a manner as to create an opening 12 in the wall of the vessel 2 and a pair of mutually opposed flaps 13 and 14 resembling doors (see FIG. 2);

b) inserting the sleeve 3 into the opening 12 in such a way that the two rigid rings 5 are accommodated internally of the corresponding cylindrical portions 2c of the blood vessel 2 on either side of the opening (see FIG. 3);

c) securing the two cylindrical portions 2c of the blood vessel 2 to the respective first rigid rings 5 by screwing each second spiral wound element 7 around the corresponding first spiral wound element 6 and along its own longitudinal axis X (see arrow F) through at least 360° about the axis of the tubular cylindrical element 3, in such a manner as to anchor a portion of the cylindrical portion 2c between the first spiral wound element 6 and the second spiral wound element 7, of which the thickness S (as already intimated) is equivalent at least to the difference between the internal diameter Di and the external diameter De respectively of the second spiral wound element 7 and of the first spiral wound element 6 (see FIGS. 4 and 6); in performing this particular step, the surgeon will take care to keep each cylindrical portion 2c pressed steadily against the relative first rigid ring 5 so as to ensure faultless contact during the stitching process; and, d) finally, flattening the two flaps 13 and 14 against the sleeve 3 and suturing the edges to encapsulate the prosthesis internally of the repair.

Figure 8:
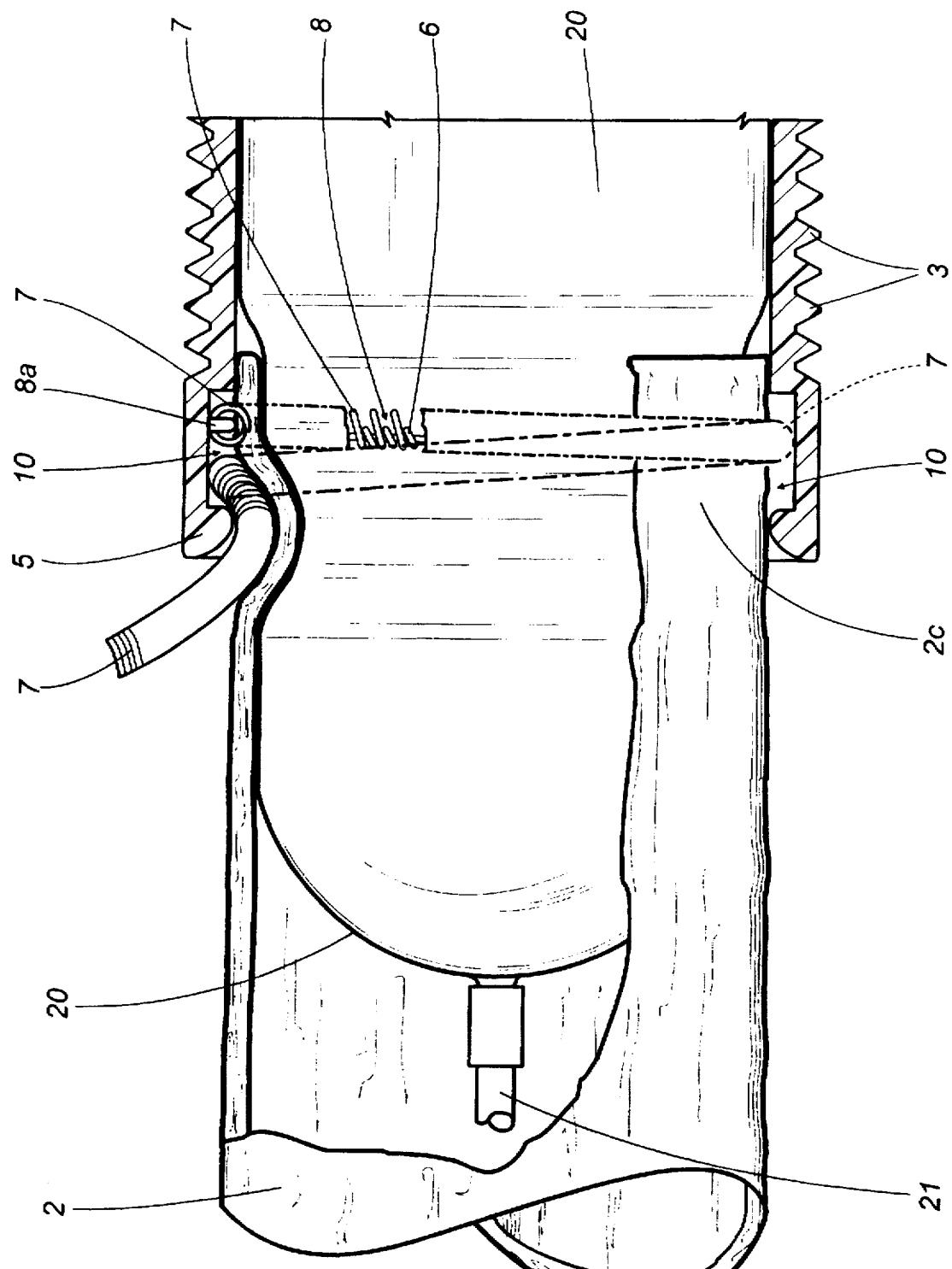

By contrast, in the event that the first spiral wound elements 6 extend circumferentially around channels 10 facing toward the inside of the sleeve, the procedure would comprise the steps of:

a) excising at least the part of the blood vessel 2 that exhibits the swelling R, in such a manner as to produce two distinct and mutually opposed open ends 2c of the healthy vessel separated by a distance L less than the longitudinal dimension of the sleeve 3 (see FIG. 7a);

b) interposing the sleeve 3 between the two open ends 2c, in such a way that each end 2c is inserted into a respective first rigid ring 5 (see FIG. 7);

c) introducing an expandable element 20 (a conventional balloon, for example, as illustrated in FIG. 8) into the blood vessel 2 at a point remote from the site of the implant, utilizing a conventional catheter 21 by means of which the element 20 can be positioned to coincide with the two open ends 2c; thereafter, inflating the element 20 first at one end and then at the other, in such a way as to establish a firm core around which the cylindrical configuration of the open ends 2c can be maintained during the subsequent step;

d) securing the two cylindrical open ends 2c of the blood vessel 2 to the respective first rigid rings 5 by screwing each second spiral wound element 7 around the corresponding first spiral wound element 6 (and along its own longitudinal axis X) through at least 360° about the axis of the tubular cylindrical element 3, in such a way that a given thickness S of the open end 2c remains anchored permanently between the first spiral wound element 6 and the second spiral wound element 7 (see FIG. 8).

In both of the procedures described above, the step of securing the ends is followed by the further step of:

e) trimming off the excess length of each second spiral wound element 7 that remains outside the dimensional compass of the sleeve 3, i.e. the part not utilized in effecting the stitching operation (see FIG. 6).

More exactly, before the sleeve 3 is offered to the cylindrical portions 2c (in the first solution illustrated) or the cylindrical open ends 2c (in the latter instance), the second spiral wound elements 7 are anchored by their sharp points 7a to the respective first spiral wound elements 6, each with the remaining length trailing loose externally of the sleeve 3.

This initial arrangement notably facilitates the task of the surgeon, who has no need to verify whether or not the second spiral wound element 7 is correctly coupled with the first spiral wound element 6 when embarking on the step of screwing the one around and along the other.

The step of screwing the second spiral wound element 7 into place is accomplished preferably by coupling the end 7b remote from the sharp point 7a with a spindle 70 connected rotatably to a power driver 71, so that the time taken to effect the stitching operation proper will be significantly minimized.

As discernible from the foregoing specification, the object stated at the outset is realized by the prosthesis disclosed with notable advantages: adopting the structural arrangement of a sleeve and two spiral wound elements, the time taken to stitch the sleeve in place is reduced markedly in comparison to earlier conventional methods, thus making a positive impact on the surgical operation as a whole; with the two spiral wound elements, moreover, the blood vessel is anchored by a succession of closely spaced stitches certain to provide a sound mechanical bond and efficiently contain the flow of blood through the vessel.

I claim:

1. A prosthesis for a blood vessel, comprising a tubular cylindrical element made of biocompatible material implantable in a section of an opened blood vessel and having a pair of first rigidly embodied rings positioned one at either end, adapted to be disposed in direct contact with corresponding cylindrical portions of the blood vessel, also a pair of first spiral wound guide and locating elements made of biocompatible material, respectively associated with and extending circumferentially around the first rigid rings through an angular distance not less than 360°, each first spiral wound element ensheathed by a respective second spiral wound stitching element made of biocompatible material having a sharp point, such that when each of the second spiral wound elements is rotated helically about the respective first spiral wound element it is advanced along its own axis and along the first spiral wound element, causing the first rigid rings to become anchored stably and continuously to the relative cylindrical portions as a given thickness of each cylindrical portion becomes interposed between the two spiral wound elements.

2. A prosthesis as in claim 1, wherein the second spiral wound element has an internal diameter greater than the external diameter of the respective first spiral wound element, such that a given thickness of the corresponding cylindrical portion can be interposed within the space afforded by the difference between the two diameters.

3. A prosthesis as in claim 1, wherein the first spiral wound element ensheaths and is permanently associated with a filiform element performing the function of a second ring extending circumferentially and externally around each of the first rigid rings and stably associated therewith through an angular distance not less than 360°.

4. A prosthesis as in claim 1, wherein the first spiral wound element ensheaths and is permanently associated with a filiform element performing the function of a second ring extending circumferentially and internally around each of the first rigid rings and stably associated therewith through an angular distance not less than 360°.

5. A prosthesis as in claim 3 or 4, wherein the filiform element is seated in a circumferential channel on the first rigid ring.

6. A prosthesis as in claim 1 wherein the tubular cylindrical element consists of a flexible sleeve with the pair of rigid rings embodied integrally one at either end.

7. A method of repairing a blood vessel affected with localized swelling by application of a prosthesis, consisting essentially of a tubular cylindrical element made of biocompatible material having a pair of first rigid rings positioned one at either end, implantable in a section of an opened blood vessel that coincides with the swelling comprising the steps of:

making incisions in the blood vessel at least at the site of the swelling, both longitudinally and around at least half the circumference of the blood vessel at respective transition areas between the swelling and a healthy portion of the vessel, in such a way as to create an opening in the wall of the vessel and a pair of mutually opposed flaps;

inserting the tubular cylindrical element into the opening in such a way that the first rigid rings are accommodated coaxially in respective cylindrical portions of the blood vessel having internal and external parts, together with respective first spiral wound guide and locating elements, made of biocompatible material, each substantially engaged with the internal part of the corresponding cylindrical portion of the blood vessel and extending circumferentially around the relative first ring;

providing respective second spiral wound stitching elements made of biocompatible material, each adapted to ensheath a relative first spiral wound element, advanceable thereon when rotated helically about its own longitudinal axis, and having a sharp point at an end;

securing the cylindrical portions of the blood vessel to the corresponding first rigid rings by screwing each second spiral wound stitching element around the corresponding first spiral element advancing the second spiral by rotating it along its own longitudinal axis and advancing the second spiral at least 360° about the axis of the tubular cylindrical element, in such a way as to anchor a portion of the cylindrical portion of the blood vessel between the first and second spiral wound elements of a thickness equivalent at least to the difference between an internal diameter of the second spiral wound element and an external diameter of the first spiral wound element;

flattening the pair of flaps against the tubular cylindrical element and suturing relative edges of the flaps one to another.

8. A method of repairing a blood vessel affected with localized swelling by application of a prosthesis, consisting essentially of a tubular cylindrical element made of biocompatible material having a pair of first rigid rings positioned one at either end, implantable in a section of an opened blood vessel that coincides with the swelling comprising the steps of:

excising at least the part of the blood vessel that exhibits the swelling, in such a way as to fashion two distinct and mutually opposed cylindrical open ends of the healthy vessel each having internal and external parts;

interposing the tubular cylindrical element between the cylindrical open ends of the blood vessel in such a way that the open ends are accommodated coaxially within the first rigid rings together with respective first spiral wound guide and locating elements made of biocompatible material, each substantially engaged with the external part of the relative cylindrical open end and extending circumferentially around the associated first ring, providing respective second spiral wound stitching elements made of biocompatible material, each adapted to ensheath a relative first spiral wound element, advanceable thereon when rotated helically about its own longitudinal axis, and having a sharp point at an end;

introducing at least one expandable element into the blood vessel, positioning the element to coincide with the site at which the first rigid rings are offered to the cylindrical open ends of the vessel, and thereupon expanding the element in such a way as to maintain a cylindrical configuration of each open end of the vessel during the subsequent step of:

securing the two cylindrical open ends of the blood vessel to the two respective first rigid rings by screwing each second spiral wound stitching element around the corresponding first spiral wound element, advancing the second spiral by rotating it along its own longitudinal axis and advancing the second spiral at least 360° about the axis of the tubular cylindrical element, in such a way as to anchor a portion of the cylindrical open end of the vessel between the first and second spiral wound elements of a thickness equivalent at least to the difference between an internal diameter of the second spiral wound element and an external diameter of the first spiral wound element.

9. A method as in claims 7 or 8, wherein the step of securing the ends is followed by the further step of:

trimming off any excess length of each second spiral wound element not utilized in the stitching operation.

10. A method as in claims 7 or 8, wherein the step of introducing the tubular cylindrical element is preceded by a preparatory step of positioning each of the second spiral wound stitching elements so that the end affording the sharp point is anchored to the respective first spiral wound element with any remaining length trailing loose outside the dimensional compass of the tubular cylindrical element.

11. A method as in claim 8, wherein the expandable element is introduced at a point of the blood vessel remote from the excised swelling.

* * * * *